United States Patent
Long

(10) Patent No.: US 9,517,139 B2
(45) Date of Patent: Dec. 13, 2016

(54) ACROMION SPACER

(75) Inventor: Jack F. Long, Warsaw, IN (US)

(73) Assignee: DePuy Synthes Products, Inc., Raynham, MA (US)

(*) Notice: Subject to any disclaimer, the term of this patent is extended or adjusted under 35 U.S.C. 154(b) by 1113 days.

(21) Appl. No.: 12/688,356

(22) Filed: Jan. 15, 2010

(65) Prior Publication Data

US 2011/0178603 A1   Jul. 21, 2011

(51) Int. Cl.
*A61F 2/40* (2006.01)
*A61F 2/30* (2006.01)

(52) U.S. Cl.
CPC ............ *A61F 2/40* (2013.01); *A61F 2/4081* (2013.01); *A61F 2002/30387* (2013.01); *A61F 2002/30616* (2013.01); *A61F 2002/30878* (2013.01); *A61F 2002/30881* (2013.01); *A61F 2002/4088* (2013.01); *A61F 2220/0025* (2013.01)

(58) Field of Classification Search
USPC .......................................... 623/19.11–19.14
See application file for complete search history.

(56) References Cited

U.S. PATENT DOCUMENTS

| | | | |
|---|---|---|---|
| 3,252,677 A | 5/1966 | Raymond | |
| 3,781,918 A | 1/1974 | Mathys | |
| 4,042,980 A | 8/1977 | Swanson et al. | |
| 4,064,568 A | 12/1977 | Grundei et al. | |
| 4,231,120 A | 11/1980 | Day | |
| 4,245,359 A | 1/1981 | Stuhmer | |
| 4,261,062 A | 4/1981 | Amstutz et al. | |
| 4,375,703 A | 3/1983 | Evans et al. | |
| 4,550,450 A * | 11/1985 | Kinnett | 623/20.11 |
| 4,725,280 A | 2/1988 | Laure | |
| 4,865,605 A | 9/1989 | Dines et al. | |
| 4,964,865 A | 10/1990 | Burkhead et al. | |
| 4,986,833 A | 1/1991 | Worland | |
| 4,990,161 A | 2/1991 | Kampner | |
| 5,032,132 A | 7/1991 | Matsen, III et al. | |
| 5,080,673 A | 1/1992 | Burkhead et al. | |
| 5,108,441 A | 4/1992 | McDowell | |
| 5,108,446 A | 4/1992 | Wagner et al. | |

(Continued)

FOREIGN PATENT DOCUMENTS

| | | |
|---|---|---|
| DE | 10164328 A1 | 7/2003 |
| EP | 0151724 | 12/1984 |

(Continued)

OTHER PUBLICATIONS

Portion of an article from Clinical Orthopaedics and Related Research, No. 176, Jun. 1983, pp. 122-123.

(Continued)

*Primary Examiner* — Marcia Watkins
(74) *Attorney, Agent, or Firm* — Maginot, Moore & Beck, LLP

(57) ABSTRACT

A prosthesis assembly for use with a scapula in one embodiment includes an acromion spacer unit, a first articulation surface on an inferior surface of the acromion spacer unit, a bone contacting surface on a superior surface of the acromion spacer unit, and a bone mounting member extending sideways from the acromion spacer unit and oriented such that when the acromion spacer unit is mounted on a scapula, the acromion spacer unit is positioned at a height above the height of a midpoint of a glenoid fossa of the scapula.

10 Claims, 6 Drawing Sheets

(56) References Cited

U.S. PATENT DOCUMENTS

| | | | |
|---|---|---|---|
| 5,489,310 | A | 2/1996 | Mikhail |
| 5,702,447 | A | 12/1997 | Walch et al. |
| 5,935,169 | A | 8/1999 | Chan |
| 5,944,757 | A | 8/1999 | Grammont |
| 6,712,854 | B2 | 3/2004 | Rogalski |
| 2003/0144738 | A1 | 7/2003 | Rogalski |
| 2004/0143336 | A1* | 7/2004 | Burkinshaw ............... 623/20.15 |
| 2006/0020344 | A1* | 1/2006 | Shultz et al. ............. 623/19.12 |
| 2006/0079963 | A1* | 4/2006 | Hansen ..................... 623/19.11 |
| 2007/0179624 | A1* | 8/2007 | Stone et al. ............... 623/19.13 |

FOREIGN PATENT DOCUMENTS

| | | |
|---|---|---|
| EP | 0581667 | 2/1994 |
| EP | 0776636 | 6/1997 |
| EP | 0963742 | 12/1999 |
| EP | 1013246 | 6/2000 |
| EP | 1064890 | 1/2001 |
| FR | 2418644 | 9/1979 |
| FR | 2578162 | 9/1986 |
| FR | 2579454 | 10/1986 |
| FR | 2704747 | 11/1994 |

OTHER PUBLICATIONS

The Roper-Day Total Shoulder Replacement, The Journal of Bone and Joint Surgery by B.A. Roper, J.M.H. Paterson, and W.H. Day, vol. 72-B, Jul. 1990.
An All-Polyethylene Cementless Tibial Component: A Five-to-Nine Year Follow-Ups Study by Kent Samuelson, M.D., and Lise Nelson, Clinical Orthopaedics and Related Research, No. 260, Nov. 1990.
International Search Report in corresponding PCT application (i.e., PCT/US2011/020658), mailed Apr. 20, 2011 (4 pages).
Unpublished Article entitled "Experimental Studies Leading to a Method for the Direct Fixation of a Polyethylene Implant to Cancellous Bone" by M.A.R. Freeman, MD, FRCS, et al., at least as early as Mar. 8, 2001 (15 pages).
Unpublished Article entitled "A Study of the Bone at the Site of Implantation of a Flanged Polyethylene PEG in the Dog" by M.A.R. Freeman, MD, FRCS, et al. At least as early as Mar. 8, 2001 (5 pages).
International Search Report in corresponding PCT application (i.e., PCT/US2011/020658), mailed Jul. 26, 2012 (6 pages).
Cementless Fixation: Using a Ployethylene Oseo-Integraton Peg as used on the Freeman-Samuelson Knee brochure, produced by Finsbury Instruments Limited London in conjunction with Adrian Tuke Limited, 1982.

\* cited by examiner

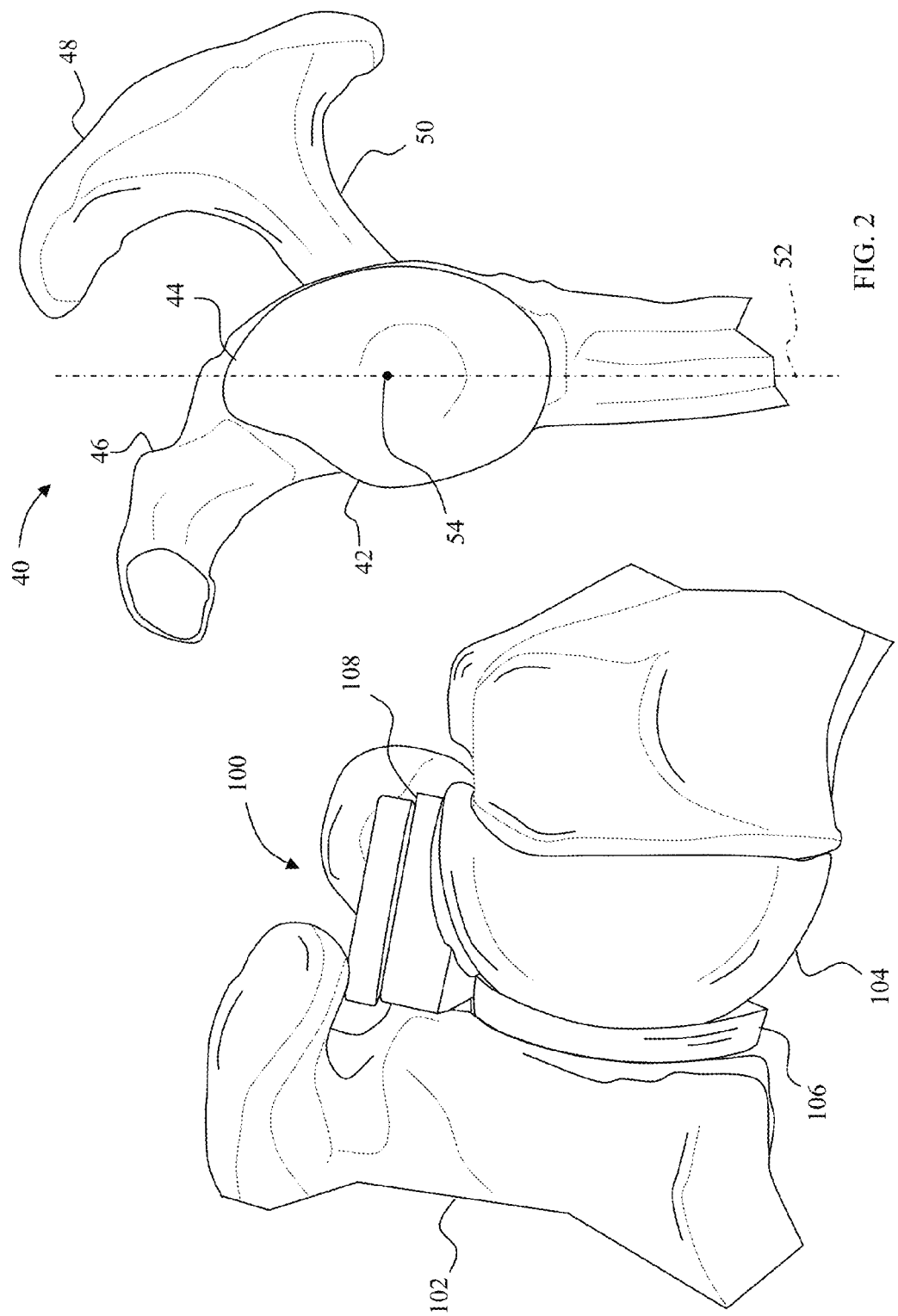

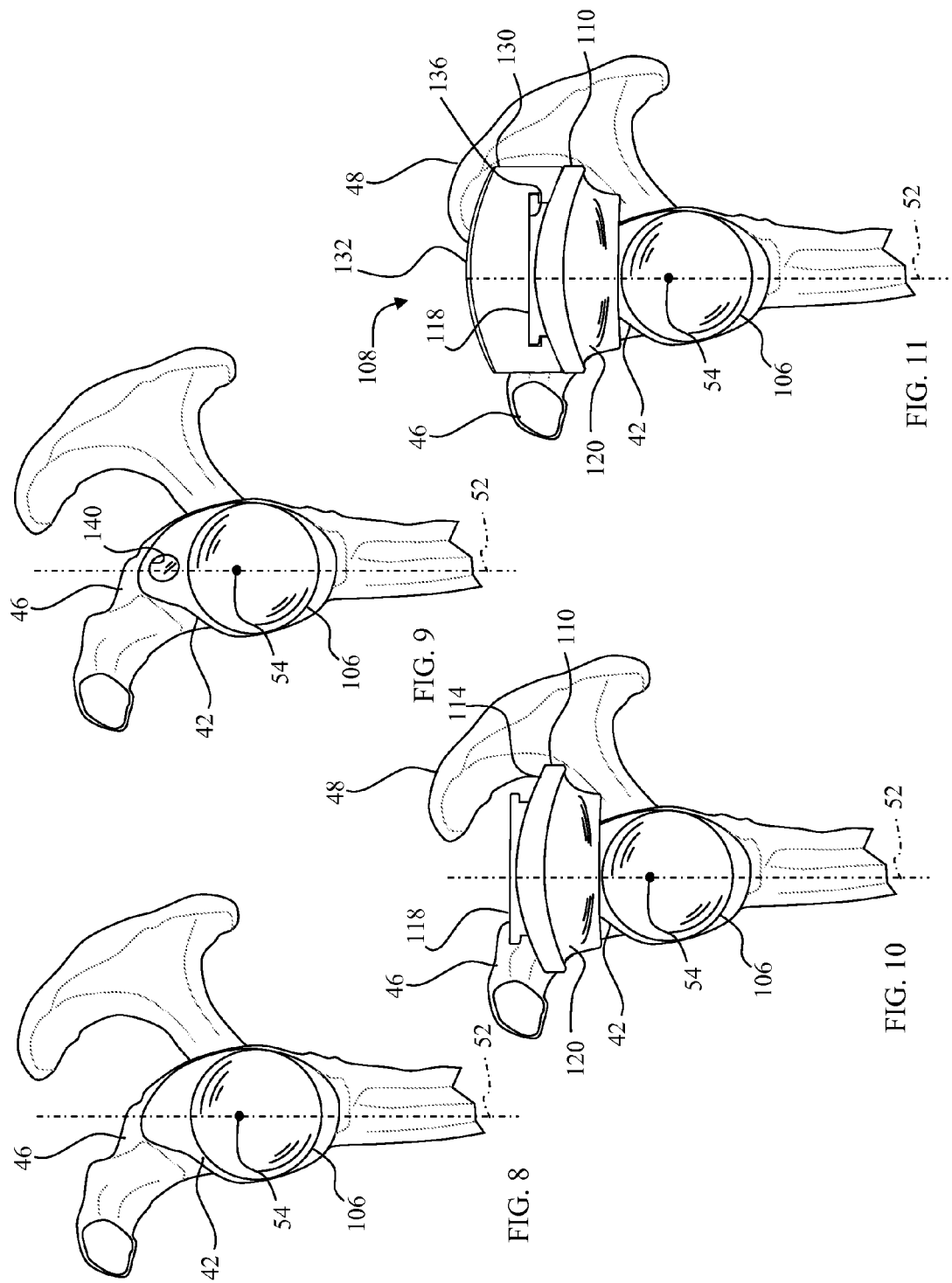

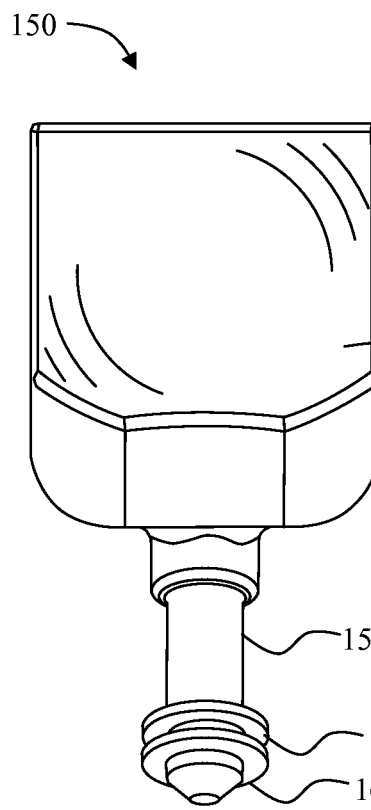
FIG. 12
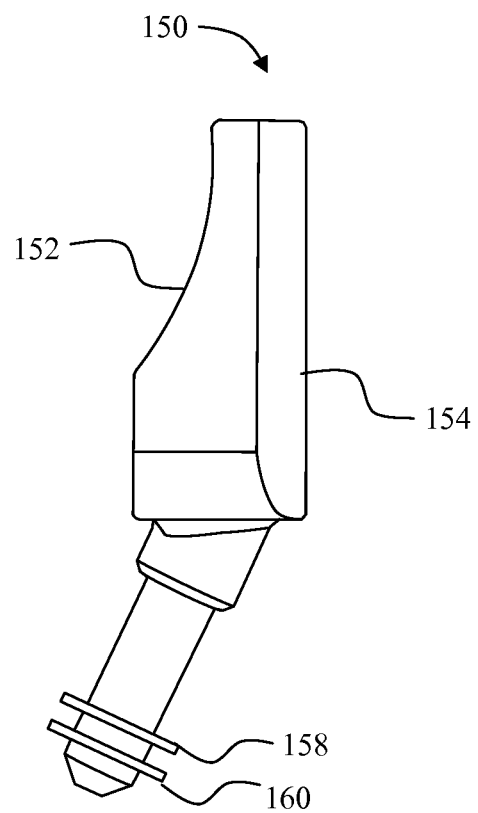
FIG. 13
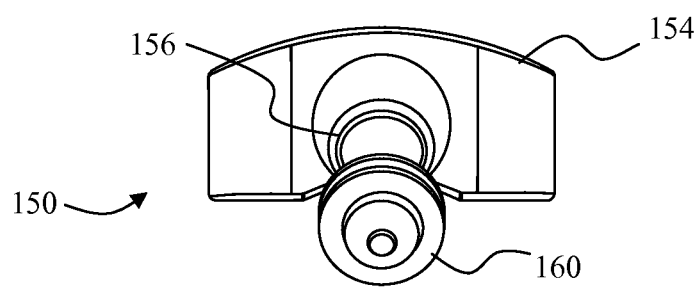

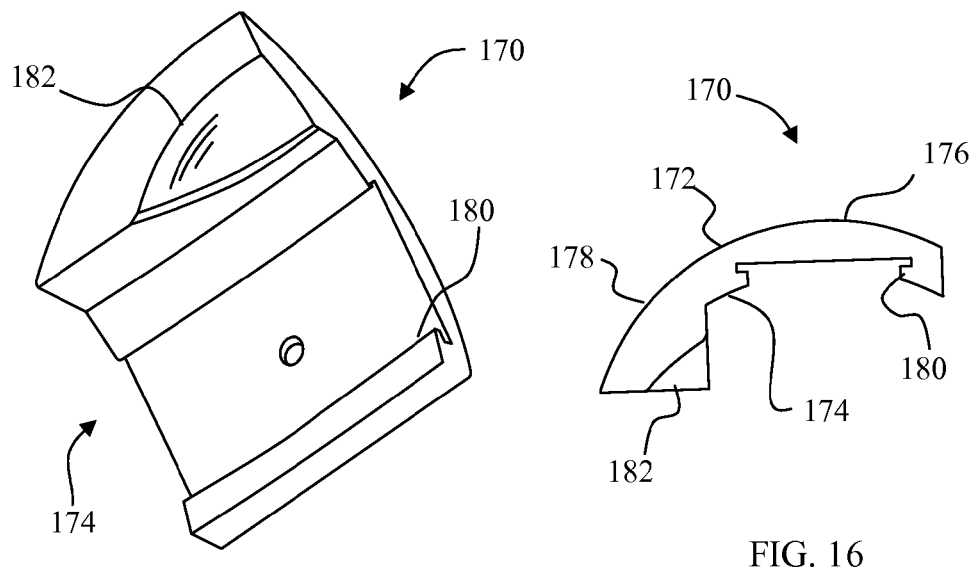
FIG. 15
FIG. 16
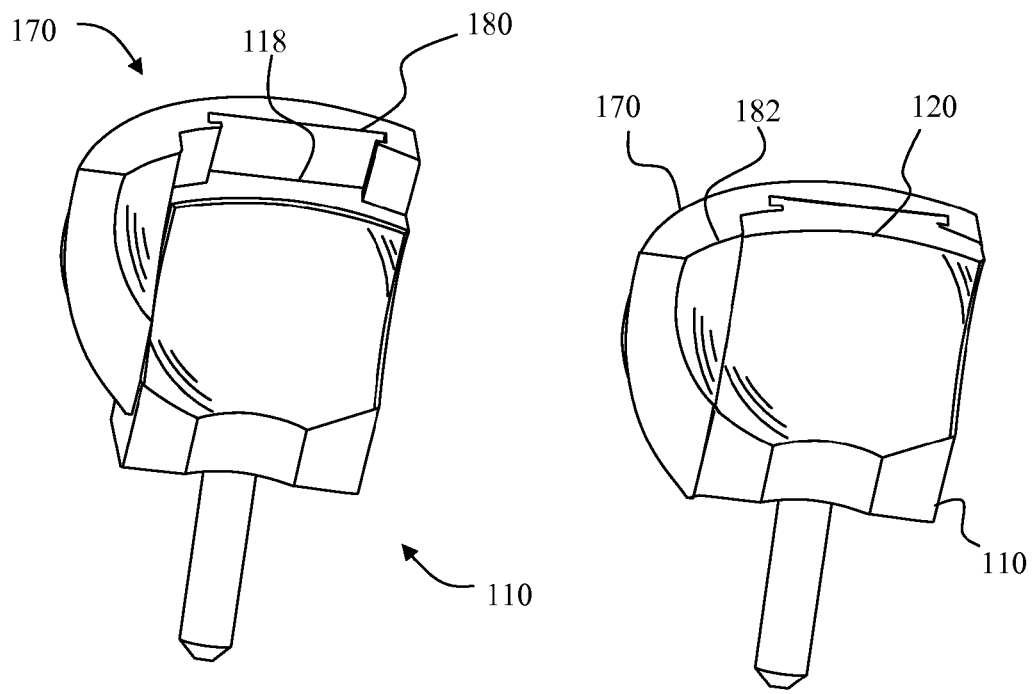
FIG. 17
FIG. 18

ACROMION SPACER

BACKGROUND

The present disclosure relates generally to shoulder prostheses, and more particularly to shoulder prostheses configured for use in shoulders having rotator cuff defects.

A typical shoulder or glenohumeral joint 10 is formed in a human body where the humerus 12 movably contacts the scapula 14 as shown in FIG. 1. The scapula 14 includes a glenoid fossa 16 that forms a socket against which the head 18 of the humerus 12 articulates. At this socket, the scapula 14 includes cartilage 20 that facilitates such articulation. Beneath the cartilage 20 is subchondral bone 22 that forms a wall of a glenoid vault 24 that defines a cavity which contains cancellous bone 26. The subchondral bone 22 that forms the glenoid vault 24 defines a glenoid rim 28 at a periphery of the glenoid vault 24 that is attached to the cartilage 20 (see FIG. 1). During the lifetime of a patient, the glenoid fossa 16 may become worn, especially at its posterior and/or superior portions thereby causing severe shoulder pain and limiting the range of motion of the patient's shoulder joint 10. To alleviate such pain and increase the patient's range of motion, a shoulder arthroplasty may be performed.

Shoulder arthroplasty often involves surgical replacement of the glenoid fossa with a conventional glenoid prosthesis such as the one disclosed in U.S. Pat. No. 6,911,047, the disclosure of which is herein incorporated by reference. The glenoid prosthesis, when implanted, provides a new laterally-facing bearing surface, which may be concave or convex, for articulation with a complementary bearing surface of a natural or prosthetic humeral head. Such conventional glenoid prosthesis is typically formed from UHMW polyethylene, titanium, or cobalt chrome and includes bone anchor(s) such as peg(s), screw(s), post(s), or a keel extending from a back side of the device opposite its bearing surface. So configured, the back side of the prosthesis is typically secured against subchondral bone of the glenoid vault while the bone anchor(s) may extend into the cavity of the glenoid vault whereby it may become anchored to cancellous bone located within the glenoid vault.

Another injury that arises is tearing of the rotator cuff. The rotator cuff is the group of muscles and their tendons that act to stabilize the shoulder. Rotator cuff tears result in a loss of function of the muscles and ligaments that control the motion of the humerus. One control of the humerus is lost, increased strain is placed on the remaining healthy muscles and ligaments increasing the potential for additional injury. Moreover, the rotator cuff limits the superior movement of the humerus. Thus, tearing of the rotator cuff allows movement of the humerus against the acromion process. Contact of the humerus against the acromion process can result in damage to both the humerus and the acromion process. This damage can be exacerbated by articulation of the humerus against the acromion process and soft tissue which are not configured to provide articulation.

A number of devices have been used to prevent superior movement of the humerus in the presence of a rotator cuff tear. U.S. Pat. No. 4,042,980, for example, discloses an artificial glenoid that includes a "step" positioned superiorly to the artificial glenoid. The step limits superior movement of a humerus. The device in the '980 patent, however, is a single "L" shaped device. Accordingly, movement of a humerus superiorly into the step generates a torque on the device which can loosen the entire device from the bone to which it is mounted. This results in a loose glenoid articulating surface which is undesirable.

Another device is disclosed in U.S. Pat. No. 5,944,757. The device disclosed in the '757 patent is a two piece system with one piece that is cemented to the acromion. Positioning of the '757 device is thus dictated by the positioning of the acromion. The acromion, however, is typically not optimally located for controlling superior movement of a humerus.

Specifically, FIG. 2 depicts a lateral view of a left scapula 40. Relative positions and locations provided herein which refer to any portion of a shoulder joint are based upon the orientation of the scapula 40 as depicted in FIG. 2. As depicted in FIG. 2, the scapula 40 includes a glenoid fossa 42 located at a base portion 44 of a coracoid process 46. The coracoid process 46 extends from the base portion 44 to a location superior and anterior of the glenoid fossa 42. An acromion 48 is connected to the base portion 44 by a spine 50. A midline 52 is depicted extending through a midpoint 54 of the glenoid fossa 42. A "midpoint" as that term is used herein is a location at about the geometric center of a glenoid fossa. As can be seen in FIG. 2, the acromion 48 is located posteriorly of the midline 52 of the glenoid fossa 42. Accordingly, when the device of the '757 patent is attached to the acromion 48, the attachment will be at location that is not directly above the mid point glenoid fossa 42. Because the device of the '757 patent is thus offset from the midline 52, the ability of the device to restrict superior movement of a humerus is reduced.

Yet another device is disclosed in U.S. Pat. No. 6,712,854. The device in the '854 patent is also positioned on the acromion and is thus not located directly above the glenoid fossa in a typical anatomy. Additionally, the device disclosed in the '854 patent is attached to the acromion using transacromial screws. This attachment technique requires access to the superior surface of the acromion process. Accordingly, in glenoid replacement procedures, an additional exposure is needed to provide access to the superior surface of the acromion.

What is needed therefore is an improved prosthesis for use in patients having deterioration of a rotator cuff including rotator cuff tears.

SUMMARY

In accordance with one embodiment of the present disclosure, there is provided a prosthesis assembly for use with a scapula including an acromion spacer unit, a first articulation surface on an inferior surface of the acromion spacer unit, a bone contacting surface on a superior surface of the acromion spacer unit, and a bone mounting member extending sideways from the acromion spacer unit and oriented such that when the acromion spacer unit is mounted on a scapula, the acromion spacer unit is positioned at a height above the height of a midpoint of a glenoid fossa of the scapula.

Pursuant to another embodiment of the present disclosure, there is provided a prosthesis kit for use with a scapula including a plurality of acromion spacer unit components, the plurality of acromion spacer unit components providing at least one first articulation surface of an acromion spacer unit, at least one bone contacting surface on a surface opposite the at least one first articulation surface of the acromion spacer unit, and at least one bone mounting member configured to extend sideways from the acromion spacer unit when the acromion spacer unit is positioned above a midpoint of a glenoid fossa of a scapula.

BRIEF DESCRIPTION OF THE DRAWINGS

FIG. 2 depicts a lateral view of a portion of a typical left scapula;

FIG. 3 depicts a shoulder prosthesis assembly including a humeral prosthesis, a glenoid prosthesis, and an acromion spacer unit implanted in a shoulder joint;

FIG. 8 depicts the scapula of FIG. 2 with a glenoid prosthesis unit implanted on the glenoid fossa such that the mid point of the glenoid fossa is covered by the glenoid prosthesis unit;

FIG. 9 depicts the scapula of FIG. 8 with a bore formed in the upper portion of the glenoid fossa and extending into the base of the coracoid process;

FIG. 10 depicts the scapula of FIG. 9 with the base portion of FIG. 4 implanted in the coracoid process using the bore of FIG. 9 at a location centered on the glenoid fossa mid line and above the mid point of the glenoid fossa;

FIG. 11 depicts the scapula of FIG. 9 with the spacer component of FIG. 5 coupled with the base portion of FIG. 4 such that a bone contacting upper surface of the spacer component is in contact with the acromion process;

FIGS. 12-14 depict an integrally formed acromion spacer unit including fins on a shaft;

FIGS. 15-16 depict a spacer component including an extension portion with an articulating surface that can be used with the base portion of FIG. 4;

FIG. 17 depicts the spacer component of FIGS. 15-16 being positioned on the base portion of FIG. 4; and FIG. 18 depicts the spacer component of FIGS. 15-16 coupled with the base portion of FIG. 4 to form an acromion spacer unit with an extended articulating surface.

DESCRIPTION OF THE PREFERRED EMBODIMENTS

Figure 1:
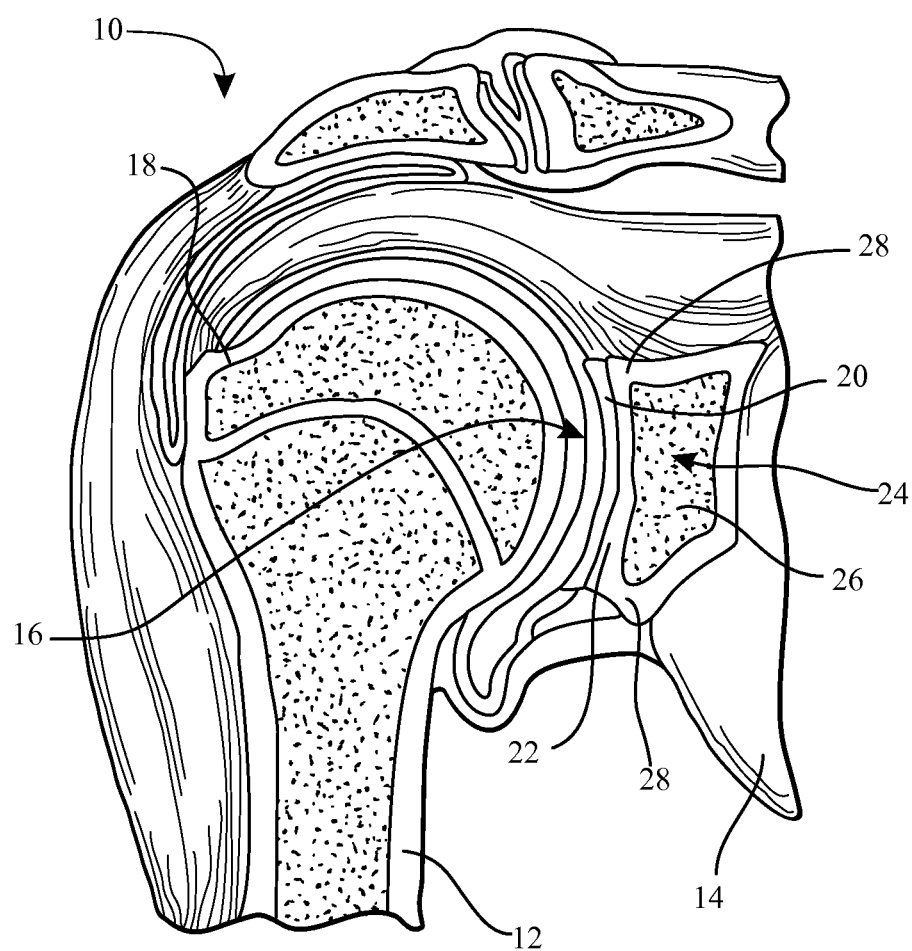
FIG. 1 depicts a cross-sectional view of an anatomically normal glenohumeral joint of a human patient.

While the shoulder prosthesis assembly described herein is susceptible to various modifications and alternative forms, specific embodiments thereof have been shown by way of example in the drawings and will herein be described in detail. It should be understood, however, that there is no intent to limit the shoulder prosthesis assembly to the particular forms disclosed, but on the contrary, the intention is to cover all modifications, equivalents, and alternatives falling within the spirit and scope of the invention as defined by the appended claims.

Referring now to FIG. 3, there is shown a shoulder prosthesis assembly 100 implanted in a shoulder joint 102. The assembly 100 includes a humeral prosthetic unit 104, a glenoid prosthetic unit 106, and an acromion spacer unit 108. Each of the humeral prosthetic unit 104, the glenoid prosthetic unit 106, and the acromion spacer unit 108 may be provided as single components or as an assembly. In one embodiment, a number of humeral prosthetic units 104, glenoid prosthetic units 106, and acromion spacer units 108 are provided in a kit. Each of the humeral prosthetic units 104, glenoid prosthetic units 106, and acromion spacer units 108 in the kit may be differently sized and shaped to allow a customized shoulder prosthesis assembly 100 to be assembled during a procedure.

Figure 4:
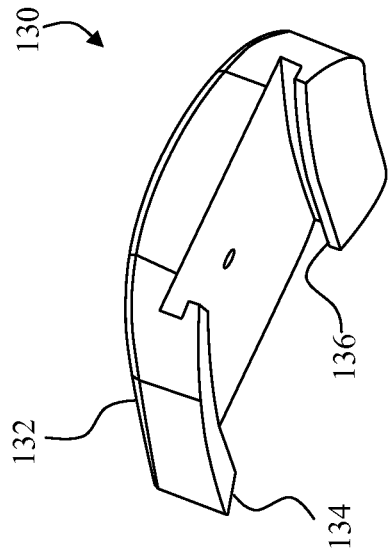
FIG. 4 depicts a bottom perspective view of the base portion of the acromion spacer unit of FIG. 3.
Figure 6:
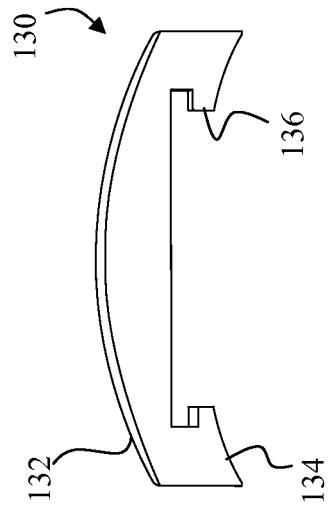
FIG. 6 depicts a bottom perspective view of the spacer component of the acromion spacer unit of FIG. 3.
Figure 5:
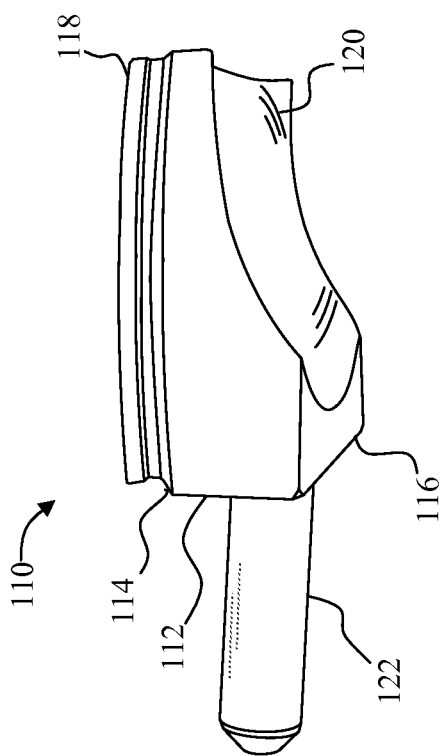
FIG. 5 depicts a plan view of the lateral end of the base portion of the acromion spacer unit of FIG. 3.
Figure 7:
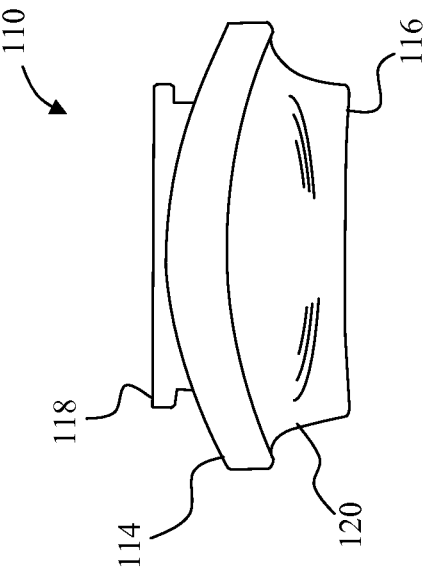
FIG. 7 depicts a plan view of the lateral end of the spacer component of the acromion spacer unit of FIG. 3.

The humeral prosthetic units 104 and the glenoid prosthetic units 106 may be of the types described in U.S. Pat. No. 6,911,047, although other types may also be used. The acromion spacer unit 108 in FIG. 3 is a modular spacer unit which is further described with reference to FIGS. 4-7. The acromion spacer unit 108 includes a base portion 110 that includes a body portion 112 with an upper surface 114 and a lower surface 116. A dovetail coupling member 118 is located on the upper surface 114 while the lower surface 116 includes an articulation surface 120. A shaft 122 extends sideways away from the body portion 112. The acromion spacer unit 108 further includes a spacer component 130 which has a curved upper surface 132, a curved lower surface 134, and a dovetail coupling member 136.

The acromion spacer unit 108 in this embodiment is made entirely of a polymer such as polyethylene. One particular polyethylene that is well suited for use in a bearing component is a high molecular weight polyethylene, for example, ultra-high molecular weight polyethylene (UHM-WPE).

In operation, the shoulder prosthesis assembly 100 is utilized in the performance of a total shoulder replacement procedure in order to provide an artificial bearing surface for the head portion of the humerus. Once a surgical site has been prepared, the glenoid area of the shoulder is exposed and the humeral prosthetic unit 104 and the glenoid prosthetic unit 106 may be installed in accordance with a desired procedure.

The acromion spacer unit 108 may also be implanted using the same surgical site that was used in implanting the humeral prosthetic unit 104 and the glenoid prosthetic unit 106. By way of example, FIG. 8 depicts the scapula 40 with the glenoid prosthetic unit 106 implanted in the glenoid fossa 42. The glenoid prosthetic unit 106 is positioned over the midpoint 54. Using the same surgical approach that was used to implant the glenoid prosthetic unit 106, a bore 140 is formed in the coracoid process 46 through the upper portion of the glenoid fossa 42 (FIG. 9). The base portion 110 is then implanted onto the coracoid process 46 by insertion of the shaft 122 into the bore 140 as depicted in FIG. 10. As shown in FIG. 10, the base portion 110 is positioned at a height above the midpoint 54 of the glenoid fossa 42. Because the base portion 110 is implanted in the coracoid process 46, the base portion 110 can be positioned directly above the glenoid fossa 42.

Once the base portion 110 is implanted, a gap exists between the upper surface 114 and the acromion 48. The gap distance, which is the distance between the upper surface 114 and the acromion process 48, will vary from individual to individual. Accordingly, a kit may be provided that includes a number of spacer components 130 with different thicknesses. Thus, a spacer component 130 of the desired thickness may be selected based upon the gap between the upper surface 114 and the acromion 48. Once selected, the spacer component 130 is coupled to the base portion 110 by insertion of the dovetail coupling member 136 onto the dovetail coupling member 118 resulting in the configuration of FIG. 11.

Once the acromion spacer unit 108 is assembled as depicted in FIG. 11, the upper surface 132 of the spacer component 130 is positioned immediately below the acromion 48 and the articulation surface 120 is positioned against the humeral prosthetic unit 104 (see FIG. 3). The articulation surface 120, along with the glenoid prosthetic unit 106, thus forms a socket portion of a socket joint against which the humeral prosthetic unit 104 articulates (see FIG. 3). When an upward force is generated on the humeral prosthetic unit 104, movement of the acromion spacer unit 108, and thus of the humeral prosthetic unit 104, is limited by contact between the upper surface 132 of the spacer component 130 with the acromion 48. Because the upper surface 132 will be forced against the acromion process 48, the upper surface 132 is convexly rounded to reduce the possibility of damage to the acromion process 48 or soft tissue located above the upper surface 132.

The implanted configuration of the shoulder prosthesis assembly 100 as depicted in FIG. 11 and FIG. 3 provides a number of benefits. By way of example, because the acromion spacer unit 108 is positioned substantially directly above the glenoid fossa 42, the potential for movement of the humeral prosthetic unit 104 past the acromion spacer unit 108 is very limited. Moreover, any upward movement of the humeral prosthetic unit 104 is limited primarily by the acromion spacer unit 108, not by the glenoid prosthetic unit 110. Thus, torque placed upon the glenoid prosthetic unit 110 is reduced since the acromion spacer unit 108 and the glenoid prosthetic unit 110 are separate as shown in FIGS. 10 and 11, and not a single "L" shaped device such as the one in U.S. Pat. No. 4,042,980. Additionally, the entire configuration of FIG. 11 and FIG. 3 can be realized using the same surgical approach used for implanting the humeral prosthetic unit 104 and the glenoid prosthetic unit 106.

While the provision of spacer components of different thicknesses allows for customization of an acromion spacer unit 108 to establish contact with the acromion 48 of individuals with different anatomical proportions, alternative embodiments provide the same capability using a kit with integrally formed acromion spacer units. By way of example, the acromion spacer unit 150 of FIGS. 12-14 is an integrally formed spacer unit. The acromion spacer unit 150 includes an articulation surface 152 and a bone contacting upper surface 154. A shaft 156 extends outwardly from one side of the acromion spacer unit 150 and includes fins 158 and 160.

The acromion spacer unit 150 may be used in the same manner as the acromion spacer unit 108. One difference between the acromion spacer unit 150 and the acromion spacer unit 108 is the inclusion of the fins 158 and 160 which enable cement-less implantation of the acromion spacer unit 150 in a coracoid process. Additionally, because the acromion spacer unit 150 is an integral unit, a shoulder prosthesis kit in one embodiment includes a plurality of acromion spacer units 150, each of the acromion spacer units 150 in the kit having a different thickness between an articulation surface 152 and a bone contacting upper surface 154. Thus, an acromion spacer unit 150 of the desired thickness is selected during surgery for implantation to provide for contact between the bone contacting upper surface 154 and the acromion process 48.

Other modifications of the acromion spacer unit 108 are also contemplated. By way of example, a bone screw may be used to attach an acromion spacer unit to a coracoid process. Additionally, spacer components may be provided which include an articulation surface that complements the articulation surface of the base portion such as the spacer component 170 of FIGS. 15 and 16. The spacer component 170 includes an outer surface 172 and an inner surface 174 opposite the outer surface 172. The outer surface 172 includes an upper bone contacting surface 176 and an extension portion 178. The inner surface 174 defines a dovetail coupling member 180 generally opposite to the bone contacting surface 176 and an articulating surface 182 generally opposite to the extension portion 178 of the outer surface 172.

The spacer component 170 may be assembled in substantially the same manner as the spacer component 130. Specifically, the spacer component 170 is coupled to the base portion 110 by insertion of the dovetail coupling member 180 onto the dovetail coupling member 118 as shown in FIG. 17. In one embodiment, the dovetail coupling member 118 and the dovetail coupling member 180 may be keyed to ensure that a left shoulder spacer component 170 is used with a left shoulder base portion 110. The dovetail coupling member 180 and the dovetail coupling member 118, for example, are curved from the end of the coupling members 118/180 closest to the glenoid fossa 42 to the end of the coupling members 118/180 farthest from the glenoid fossa 42. The curvature of the dovetail coupling member 180 is shown most clearly in FIG. 15.

As the spacer component 170 is fully coupled with the base portion 110, the articulating surface 182 is positioned adjacent to the articulating surface 120 as shown in FIG. 18. The extended articulating surface formed by the articulating surface 182 and the articulating surface 120 may be used to ensure entrapment of the humeral prosthetic unit 104 even if there had been extensive damage to the soft tissue in a shoulder. A number of different spacer components 170 may be provided with differing amounts of additional articulating surface and different thicknesses to provide a configuration that is optimized for a particular procedure.

There are several advantages arising from the various features of each of the embodiments of the shoulder prosthesis assembly described herein. It will be noted that alternative embodiments of the shoulder prosthesis assembly may not include all of the features described yet still benefit from at least one or more of the advantages of such features.

Moreover, even if provided in a shoulder prosthesis kit including glenoid prostheses and humeral prostheses, the acromion prosthetic units may be implanted without implanting either a glenoid prosthesis or a humeral prosthesis. Furthermore, while the various embodiments include a single bone mounting member, additional bone mounting members could be used to mount the acromion prosthetic units to the coracoid process. Additionally, the acromion prosthetic units may further be attached to the acromion using one or more bone mounting members such as screws to provide additional fixation points.

Those of ordinary skill in the art may readily devise their own implementations of the shoulder prosthesis assembly that incorporates one or more of the features and fall within the spirit and scope of the present invention as defined by the appended claims.

What is claimed is:
1. A prosthesis assembly for use with a scapula, comprising:
an acromion spacer unit configured such that when mounted on a scapula, the acromion spacer unit is separate from any component implanted at a midpoint of a glenoid fossa of the scapula such that a force against the mounted acromion spacer unit is not transferred to the component implanted at the midpoint;
a first articulation surface on an inferior surface of the acromion spacer unit;

a bone contacting surface on a superior surface of the acromion spacer unit; and a bone mounting member extending sideways from the acromion spacer unit and oriented such that when the acromion spacer unit is mounted on a scapula, the bone mounting member extends medially from the acromion spacer unit through an upper portion of the glenoid fossa and the acromion spacer unit is positioned at a height above a height of the midpoint of the glenoid fossa of the scapula.

2. The assembly of claim 1, wherein the acromion spacer unit further comprises:

a base portion from which the bone mounting member extends, the base portion including a coupling member configured to couple with a complementary coupling member on a spacer component which defines the bone contacting surface.

3. The assembly of claim 2, wherein the base portion coupling member comprises a dovetail coupling member.

4. The assembly of claim 1, further comprising:

a glenoid prosthesis unit configured such that when the acromion spacer unit is mounted on the scapula and the glenoid prosthesis unit is implanted in the glenoid fossa, the acromion spacer unit component is disconnected from the glenoid prosthesis unit.

5. The assembly of claim 1, further comprising:

a humeral prosthesis.

6. A prosthesis kit for use with a scapula, comprising:

a plurality of acromion spacer unit components, the plurality of acromion spacer unit components providing at least one first articulation surface of an acromion spacer unit configured to be movable with respect to any component located at a midpoint of a glenoid fossa of a scapula when the acromion spacer unit is mounted on the scapula such that a force against the mounted acromion spacer unit is not transferred to the component located at the midpoint, at least one bone contacting surface on a surface opposite the at least one first articulation surface of the acromion spacer unit, and at least one bone mounting member configured to extend sideways from the acromion spacer unit through an upper portion of the glenoid fossa when the acromion spacer unit is positioned above the midpoint of the glenoid fossa of the scapula.

7. The kit of claim 6, further comprising:

at least one glenoid prosthesis unit, the at least one glenoid prosthesis unit configured such that when a first of the plurality of acromion spacer unit components is mounted on the scapula and a first of the at least one glenoid prosthesis units is implanted in a glenoid fossa, the first of the plurality of acromion spacer unit components is disconnected from the first of the at least one glenoid prosthesis units.

8. The kit of claim 7, further comprising:

at least one humeral prosthesis unit.

9. The kit of claim 6, wherein:

the at least one first articulation surface is defined by a base portion;

the base portion includes a first coupling member; and the at least one bone contacting surface comprises a plurality of bone contacting surfaces, each of the plurality of bone contacting surfaces defined by a respective one of a plurality of spacer components.

10. The kit of claim 9, wherein the first coupling member comprises a dovetail coupling member.

* * * * *